United States Patent
Pohl et al.

(10) Patent No.: US 7,511,176 B2
(45) Date of Patent: Mar. 31, 2009

(54) PROCESS FOR THE PREPARATION OF TOLUENEDIAMINES BY CATALYTIC HYDROGENATION OF DINITROTOLUENES

(75) Inventors: Fritz Pohl, Brunsbüttel (DE); Wolfgang Lorenz, Dormagen (DE); Lars Padeken, Düsseldorf (DE); Bernd Pennemann, Bergisch Gladbach (DE); Friedhelm Steffens, Leverkusen (DE); Gerhard Wiechers, Leverkusen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/001,879

(22) Filed: Dec. 13, 2007

(65) Prior Publication Data

US 2008/0146847 A1    Jun. 19, 2008

(30) Foreign Application Priority Data

Dec. 19, 2006  (DE) .................... 10 2006 060 572

(51) Int. Cl.
*C07C 209/00* (2006.01)
*C07C 205/00* (2006.01)

(52) U.S. Cl. .................... 564/422; 564/420; 568/934

(58) Field of Classification Search ................ 564/420, 564/422; 568/934

See application file for complete search history.

(56) References Cited

U.S. PATENT DOCUMENTS

| 3,356,728 A | 12/1967 | Cimerol et al. | 260/580 |
|---|---|---|---|
| 3,499,034 A | 3/1970 | Gonzalez | 260/580 |
| 4,224,249 A | 9/1980 | Kunz et al. | 260/580 |
| 4,482,769 A | 11/1984 | Toseland et al. | 568/934 |
| 4,935,557 A | 6/1990 | Carr et al. | 568/934 |
| 5,756,867 A * | 5/1998 | Hermann et al. | 568/934 |
| 2004/0073066 A1 * | 4/2004 | Zehner et al. | 564/416 |
| 2004/0267061 A1 * | 12/2004 | Dieterich et al. | 568/934 |

FOREIGN PATENT DOCUMENTS

| EP | 0019454 A2 | 11/1980 |
|---|---|---|
| GB | 832153 | 4/1960 |

* cited by examiner

*Primary Examiner*—Jafar Parsa
(74) *Attorney, Agent, or Firm*—Noland J. Cheung; N. Denise Brown

(57) ABSTRACT

The present invention relates to a process for the preparation of toluenediamine, in which dinitrotoluene is reacted with hydrogen in the presence of a catalyst. The dinitrotoluene required by this process has a content of carbon dioxide, in either physically dissolved or chemically bonded form, of not more than 0.175 mol %, based on the molar amount of the dinitrotoluene.

5 Claims, No Drawings

PROCESS FOR THE PREPARATION OF TOLUENEDIAMINES BY CATALYTIC HYDROGENATION OF DINITROTOLUENES

CROSS REFERENCE TO RELATED PATENT APPLICATION

The present patent application claims the right of priority under 35 U.S.C. §119 (a)-(d) of German Patent Application No. 10 2006 060 572.1, filed Dec. 19, 2006.

BACKGROUND OF THE INVENTION

The present invention relates to a process for the preparation of toluenediamine (TDA), in which dinitrotoluene (DNT) is reacted with hydrogen in the presence of a catalyst, wherein the dinitrotoluene used has a content of carbon dioxide in physically dissolved or chemically bonded form of not more than 0.175 mol %, based on the molar amount of the dinitrotoluene used.

Toluenediamines are intermediates for the preparation of toluene diisocyanates (TDI), which are important preliminary products, produced on a large scale, for the preparation of polyurethanes. Their preparation by catalytic hydrogenation of dinitrotoluenes (DNT) is known and has often been described (see, for example, Ullmann's Enzyklopädie der technischen Chemie, 4th Edition, Volume 7, page 393 ff, 1973, Verlag Chemie Weinheim/New York). The industrial production of toluenediamines is carried out predominantly by reaction of a mixture of isomeric dinitrotoluenes that is obtainable by nitration of toluene with nitric acid. Commercial mixtures of isomeric dinitrotoluenes are produced predominantly in the form of crude DNT in a two-stage isothermal nitration process using nitric acid in the presence of sulfuric acid as catalyst, with the formation of the corresponding mononitrotoluenes as intermediates. They are subsequently worked up in stages provided downstream of the reaction, predominantly in washing stages, and thus largely freed of dissolved sulfuric acid and nitric acid, and also of secondary components such as, for example, cresols and their degradation products, formed in the reaction stages.

Typical commercial DNT products have DNT contents >98.5% by weight, less than 0.1% by weight of mononitrotoluene, less than 0.1% by weight of trinitrotoluene and less than 0.1% by weight of other secondary components, as well as small residual amounts of toluene, based on the total weight of the DNT product mixture, with DNT yields of >98% and toluene conversions of >99.9%. Also important is the weight ratio of the total amount of the 2,4- and 2,6-DNT isomers to the total amount of the 2,3-, 3,4-, 2,5- and 3,5-DNT isomers. According to commercial specifications, the total content of 2,4- and 2,6-DNT isomers in the crude DNT is >95% by weight, based on the total weight of the crude DNT. The content of 2,4-DNT is preferably from 79.0% to 81.0% by weight, based on the sum of the weights of 2,4-DNT and 2,6-DNT. Accordingly, the content of 2,6-DNT is from 19.0% to 21.0% by weight, based on the sum of the weights of 2,4-DNT and 2,6-DNT.

The catalytic hydrogenation of these commercial DNT products can be carried out with the concomitant use of an inert solvent or without a solvent, the mixtures then being melted before the hydrogenation is carried out. It can be carried out either discontinuously or continuously using conventional reactors. In addition to a continuous reaction procedure, the selectivities of the reaction that can be achieved with the process being used, and the capacities and working lives of the catalysts used, are especially important to the economic success of the process that is used.

U.S. Pat. No. 3,356,728 discloses an improved continuous process for the preparation of aromatic amines by catalytic hydrogenation of aromatic polynitro aromatic compounds in a sludge phase reactor, in which the process is explained using the example of the reaction of dinitrotoluene. According to the teaching of U.S. Pat. No. 3,356,728, the catalytic hydrogenation of dinitrotoluene in this reaction system is carried out very effectively in terms of selectivity, catalyst working life and throughput if the reaction zone is always saturated with hydrogen during the reaction, the aromatic polynitro compound is added to the system while maintaining a specific weight ratio to the catalyst present in the reaction system (i.e. "catalyst loading"), and the concentration of the added aromatic polynitro compound in the reaction zone does not exceed a given limiting value.

U.S. Pat. No. 3,356,728 claims a working range <0.15, and preferably a working range from 0.01 to 0.11, for the so-called catalyst loading (i.e. "ratio of the added amount of aromatic polynitro compound in kg equivalents of nitro groups per hour to the catalyst present in the reactor in kg"). It also discloses that the maximum concentration of aromatic nitro compound to be maintained in the reaction mixture is 0.1% by weight, and preferably less than 0.015% by weight, based on the weight of the reaction mixture.

According to the teaching of U.S. Pat. No. 3,356,728, the claimed catalyst loadings lead to high concentrations of active catalyst in the reaction system, such that the aromatic polynitro compound which is fed in is immediately reacted to the desired amine after entering the mixture, and the concentration of unreduced nitro compound in the reaction system is thereby kept below 0.005% by weight at all times. As disclosed in U.S. Pat. No. 3,356,728, this low concentration prevents the catalyst from rapidly being poisoned and, in addition, higher yields and improved product purity are obtained at substantially reduced costs in the reaction of the aromatic polynitro compound.

The avoidance of inadmissibly high concentrations of unreduced nitro compound in the reaction mixture of catalytic hydrogenations of aromatic polynitro compounds is also the subject-matter of U.S. Pat. No. 3,499,034. U.S. Pat. No. 3,499,034 discloses 0.5% by weight, based on the weight of the reaction mixture, as the maximum concentration of unreduced aromatic nitro compounds that is to be maintained. According to the teaching of U.S. Pat. No. 3,499,034, these low concentrations of unreduced nitro compound especially bring about low concentrations of the azoxy, azo and hydrazo compounds which, as is known, are also formed in the catalytic hydrogenation of nitro compounds and which, as described in U.S. Pat. No. 3,499,034, constitute tar-like compounds, which can be reduced but only with difficulty and only with a marked slowing down of the desired catalytic hydrogenation of the aromatic polynitro compound.

According to the teaching of EP 0 171 052 B1, the formation of tar-like intermediates in the catalytic hydrogenation of aromatic nitro compounds is dependent not only on the concentration of unreduced nitro compound but also on the nitro compound itself. As disclosed in EP 0 171 052 B1, the catalytic hydrogenation of aromatic nitro compounds is particularly successful if mixtures of at least 25% by weight of mononitro-nonamino aromatic compounds with at least 25% by weight of dinitro- or mononitro-amino aromatic compounds are used as the aromatic nitro compounds. The advantage of the disclosed reaction procedure is limited, however, in view of the outlay that it is subsequently necessary to separate the hydrogenation products by distillation. Thus, the catalytic hydrogenation of aromatic polynitro compounds on a large scale is conventionally carried out in accordance with the principles outlined by way of example in U.S. Pat. No. 3,356,728 and U.S. Pat. No. 3,499,034.

According to the teaching of GB Patent 832,153, the desired catalytic hydrogenation of the nitro compound can be greatly affected not only by the unreduced aromatic nitro compound and its intermediate azoxy, azo and hydrazo compounds, but also by contaminants contained in the nitro compound to be hydrogenated. As disclosed in GB Patent 832, 153, nitrophenols and nitrocresols, which are usually present in small amounts in commercial dinitrotoluene isomeric mixtures, are decomposition accelerators as well as strong catalyst poisons, so their concentration is to be regarded as critical in respect of process safety and in respect of the efficiency of the desired catalytic hydrogenation of the nitro compound to the corresponding amine. According to the teaching of GB Patent 832,153, the nitro compound used in the catalytic hydrogenation should contain less than 500 ppm "nitrophenols", preferably less than 20 ppm "nitrophenols", with the term "nitrophenols" being understood according to GB Patent 832,153 as the sum of nitrophenol- and nitrocresol-like compounds.

EP 0 019 454 B1 also deals with the influence of nitrophenol-like contaminants. According to the teaching of EP 0 019 454 B1, the removal of the nitrophenol-like contaminants is largely unnecessary, but it is important in the catalytic hydrogenation of commercial dinitrotoluenes, in order to avoid catalyst poisoning and the decomposition of the amine that is formed, to lower their acid content, expressed as HNO3, to below 6000 ppm, based on the weight of the dinitrotoluene. EP 0 019 454 B1 discloses a process in which the crude dinitrotoluene is washed only with water; aqueous alkaline solutions are not used for removing nitrophenol-like contaminants.

The statements made in U.S. Pat. No. 4,482,769 are more differentiated. According to the teaching therein, washing of commercial dinitrotoluene mixtures with aqueous alkaline solutions is advantageous, but the washing should be carried out in such a manner that the aqueous phase has a pH value in the range from 5.8 to 6.4. As disclosed in U.S. Pat. No. 4,482,769, the result of such a pH value in the washing is that all the acidic components are largely removed from the dinitrotoluene, with only 2,4-dinitroorthocresol, which is poorly biodegradable, remaining in the dinitrotoluene as a secondary component. According to the teaching of U.S. Pat. No. 4,482, 769, on the one hand the influence of acidic components is advantageously prevented by the claimed process, and on the other hand a low content of 2,4-dinitroorthocresol does not affect subsequent hydrogenations of the dinitrotoluene so prepared.

Surprisingly, it has now been found that in the preparation of toluenedianine, in which dinitrotoluene is reacted with hydrogen in the presence of a catalyst, the desired reaction is substantially influenced not only by the parameters known according to the prior art, but also by the carbon dioxide content of the dinitrotoluene used in the reaction. More specifically, substantially better catalyst working lives are obtained, while the selectivity of the reaction is increased, if the carbon dioxide contents of the dinitrotoluene are low.

SUMMARY OF THE INVENTION

The present invention provides a process for the preparation of toluenediamine, in which dinitrotoluene is reacted with hydrogen in the presence of a catalyst, characterised in that the dinitrotoluene used has a content of carbon dioxide in physically dissolved or chemically bonded form of less than 0.175 mol %, based on the molar amount of the dinitrotoluene used.

A suitable analytical method to determine the content of carbon dioxide in physically dissolved or chemically bonded form, which can be used within the scope of the process according to the invention, is disclosed and described in detail in the "Examples" section below, under the title "Description of the analytical method for the quantitative determination of carbon dioxide in physically dissolved or chemically bonded form in dinitrotoluene". Within the scope of this invention, the content of carbon dioxide in physically dissolved or chemically bonded form is to be understood as meaning the total content of carbon dioxide, which can be present in physically dissolved and/or chemically bonded form.

In a preferred embodiment of the invention, the process for the preparation of toluenediamine comprises:

a) reacting toluene with nitrating acid to form a reaction mixture containing mononitrotoluenes, b) separating the reaction mixture containing mononitrotoluenes into an organic phase containing mononitrotoluenes and an aqueous phase containing sulfuric acid, c) reacting the organic phase containing mononitrotoluenes with nitrating acid, to yield a reaction mixture containing dinitrotoluenes (i.e. an isomeric mixture of dinitrotoluenes)

d) separating the reaction mixture containing dinitrotoluenes into an organic phase containing dinitrotoluenes and an aqueous phase containing sulfuric acid, e) purifying the organic phase containing dinitrotoluenes with water in a multi-stage extraction in which each stage comprises mixing and phase separation, to yield an isomeric mixture of dinitrotoluenes which contains (i) from 74% to 81% by weight of 2,4-DNT, (ii) from 17% to 21% by weight of 2,6-DNT, and (iii) less that 5.5% by weight of 2,3-DNT, 2,5-DNT, 3,4-DNT and 3,5-DNT combined, with the sum of (i), (ii) and (iii) totalling 100% by weight of dinitrotoluene, f) reacting the resultant isomeric mixture of dinitrotoluenes with hydrogen in the presence of a catalyst to form toluenediamines, wherein (1) the dwell time (residence time) for the mixing in each stage of the multi-stage extraction in step e) is at least 4 minutes and not more than 60 minutes, and (2) an inert gas is additionally introduced into the mixture of the organic phase containing dinitrotoluenes and water in at least the last stage of the extraction in step e), with the weight ratio of inert gas to dinitrotoluenes being such that the resultant purified dinitrotoluenes have a total content of carbon dioxide in physically dissolved or chemically bonded form of less than 0.175 mol %, preferably of less than 0.125 mol %, and most preferably of less than 0.075 mol %, based on the molar amount of the dinitrotoluenes.

DETAILED DESCRIPTION OF THE INVENTION

In the process according to the invention, and in particular in its preferred embodiment (i.e. steps a) to g) as described above), the reaction in the preparation of the mononitrotoluenes in step a) and of the dinitrotoluenes in step c) can be carried out either adiabatically or isothermally. It is preferably carried out isothermally using cooled stirrer vessel cascades through which the reaction mixture flows continuously or series-connected cooled loop reactors, such as are described in, for example, EP 0 903 336 B1, which is believed to correspond to U.S. Pat. No. 5,902,910, the disclosure of which is hereby incorporated by reference, or DE10 2004 005 913 A1. Static and dynamic separators can be used in the phase separation as in steps b) and d). Preference is given to the use of static separators as are described in, for example, in EP 0 903 336 B1, which is believed to correspond to U.S. Pat. No. 5,902,910, the disclosure of which is hereby incorporated by reference.

In the preferred process of the invention, the multi-stage extraction in step e) of the organic phase obtained in step d) can be carried out with recovery of the principal amount of the nitric acid and/or sulfuric acid contained in the organic phase. The recovery can be carried out by a single- or multi-stage procedure using small amounts of uncharged water in the individual stages, or by a multi-stage procedure, counter-currently, using larger amounts of water which are circulated through each stage. Suitable processes are described in, for example, EP 0 279 312 B1 or EP 0 736 514 B1, which are believed to correspond to U.S. Pat. Nos. 5,001,286 and 5,756,867, respectively, and the disclosures of which are hereby incorporated by reference.

There is preferably no recovery of acid. Then, in the preferred process according to the invention, the dinitrotoluene-containing organic phase obtained in step d) is washed in step e) with water in a multi-stage extraction that comprises mixing and phase separation in each stage. In a particularly preferred embodiment, the water used for the multi-stage extraction of the dinitrotoluenes (i.e. the isomeric mixture of dinitrotoluene) can have different pH values in the different stages. It is then preferred in step e) for the extraction of the dinitrotoluenes to use alkaline water in at least one stage and neutral water in at least one stage. In the case of an extraction comprising more than two stages, it is preferred to use alkaline water in at least one stage, acidic water in at least one stage and neutral water in at least one stage. In this preferred embodiment, the extraction in the stages is carried out as a "liquid/liquid" extraction. This is ensured by suitably choosing the temperatures of the dinitrotoluenes used and of the aqueous phases used as the extraction agents.

In a further preferred embodiment, the multi-stage extraction is carried out in at least one stage using an apparatus for mixing and separating liquids of different specific gravities that are virtually insoluble in one another, as is described in, for example, DE-B-1 135 425, which is believed to correspond to U.S. Pat. No. 3,162,510, the disclosure of which is hereby incorporated by reference.

Characteristic features of the apparatus described in DE-B-1 135 425, which is believed to correspond to U.S. Pat. No. 3,162,510, the disclosure of which is hereby incorporated by reference, are a mixing zone in the form of an extraction or washing column, having a chamber for phase separation arranged concentrically around the mixing zone, the mixture that leaves the mixing zone entering the chamber via an overflow with a surrounding hollow jacket of the "cut-off" washing column and being separated into two phases on the basis of density. In order to allow the apparatus described in DE-B-1 135 425 (which is believed to correspond to U.S. Pat. No. 3,162,510, the disclosure of which is hereby incorporated by reference) in column 2/lines 35-52 and column 3/lines 1-12 in respect of its structure and in column 3/lines 29-47, in respect of its function to be used advantageously in the process according to the invention, a possibility for the supply of inert gas into the mixing zone, for example through an additional opening in the region of the bottom of that portion of the apparatus, should additionally be provided in the apparatus.

It is, however, possible in principle to use for the extraction in the purification step e), any form of multi-stage extraction process and extraction apparatus comprising mixing and phase separation in each stage, provided that the dwell time or residence time for the mixing (i.e. the time period during which the mixture is performed) in each stage of the extraction within step e) is at least 4 minutes and not more than 60 minutes (see requirement (1) in the preferred process above); and that an inert gas is additionally introduced into the mixture of the organic phase containing dinitrotoluenes and water in at least in the last stage of the extraction within step e) (see requirement (2) in the preferred process above). The weight ratio of inert gas to dinitrotoluenes is such that the resultant purified dinitrotoluenes have a total content of carbon dioxide in physically dissolved or chemically bonded form of less than 0.175 mol %, based on the molar amount of the dinitrotoluenes.

The required amount or the required weight ratio of inert gas to the dinitrotoluenes can readily be determined by the person of ordinary skill in the art. This amount or ratio is readily determined by simple experimentation, by carrying out tests with increasing amounts or weight ratios of inert gas to dinitrotoluenes until the required content of carbon dioxide in physically dissolved or chemically bonded form is reached.

The loading of the dinitrotoluene isomeric mixtures with carbon dioxide in physically dissolved or chemically bonded form that is achieved after the multi-stage extraction within the purification step e) can preferably be monitored by gas chromatography by means of "headspace GC". A suitable analytical method for determining the content of carbon dioxide in physically dissolved or chemically bonded form, which can preferably be used within the scope of the process according to the invention, is disclosed in the instant application in the section titled "Description of the analytical method for the quantitative determination of carbon dioxide in physically dissolved or chemically bonded form in dinitrotoluene".

The dinitrotoluenes (dinitrotoluene isomeric mixture) so prepared are preferably collected in a receiver and fed therefrom in liquid form to the hydrogenation, which is preferably carried out continuously. The dinitrotoluenes that preferably flow continuously to the receiver can be subjected to a further stripping gas treatment or a different type of carbon dioxide removal either before they are collected in the receiver, after they are in the receiver, or after they have been removed from the receiver. The only important factor for the process according to the invention is that the dinitrotoluene used in the catalytic hydrogenation for the preparation of toluenediamine has a content of carbon dioxide in physically dissolved or chemically bonded form of less than 0.175 mol %, based on the molar amount of the dinitrotoluene used.

The catalytic hydrogenation of the dinitrotoluene so prepared can be carried out with the concomitant use of an inert solvent or without a solvent. It is preferably carried out without a solvent using an aqueous catalyst suspension. It can be carried out either discontinuously or continuously using conventional reactors. Examples thereof are stirrer vessels, bubble columns or loop reactors, such as loop-Venturi reactors, or jet loop reactors with an internal and external circuit.

In a preferred embodiment of the process according to the invention, a jet loop reactor with an internal and external circuit is used, as is described, for example, in EP 1 137 623 B1, which is believed to correspond to U.S. Pat. No. 6,350,911, the disclosure of which is hereby incorporated by reference.

In a further preferred form of the process according to the invention, the catalytic hydrogenation of the dinitrotoluene having a content of carbon dioxide in physically dissolved or chemically bonded form of less than 0.175 mol %, based on the molar amount of the dinitrotoluene used, is carried out in a sludge phase reactor having an integrated heat exchanger such as is described in, for example, WO-A-96/11052, which is believed to correspond to U.S. Pat. No. 5,779,995, the disclosure of which is hereby incorporated by reference. This reactor has, as the heat exchanger, an annular chamber which is covered at the bottom and top by the reaction mass in the reactor, the annular chamber having a plurality of vertical flow channels for the reaction mass and the coolant flowing through the annular chamber between the flow channels for the reaction mass. As disclosed in WO-A-96/11052 which is believed to correspond to U.S. Pat. No. 5,779,995, the disclosure of which is hereby incorporated by reference, this reactor is particularly suitable for dissipating the heat of reaction that is liberated during the catalytic hydrogenation of the dinitrotoluene mixtures in the form of usable steam. In the catalytic hydrogenation of the dinitrotoluene according to the invention, an operating temperature of from 80 to 200° C., preferably from 100 to 180° C., and a pressure of from 5 to 100 bar, preferably from 10 to 50 bar, are maintained in the reactor.

The supply of hydrogen to the system is preferably carried out in such a manner that the stoichiometric hydrogen requirement for the reaction of the nitro group equivalents that are fed in to the corresponding amine compounds is always covered and, in addition, the contents of the reactor are always saturated with hydrogen, taking particular account of the surface areas of the catalyst(s) used. This is preferably achieved by providing the sludge phase reactor that is preferably used with a gassing stirrer, by means of which a largely homogeneous, fine distribution of the catalyst(s) suspended in the reaction mixture and of the hydrogen in the form of finely dispersed hydrogen bubbles in the reaction mixture is produced.

According to the teaching of U.S. Published Patent Application 2004/0073066 A1, it is advantageous to adjust the purity of the hydrogen present in the reactor to from 50 to 97 vol %, preferably from 70 to 97 vol %, and most preferably from 80 to 95 vol %, by the addition of inert compounds that are gaseous under the hydrogenation conditions or by establishing an appropriate purge gas stream for discharging the gaseous contaminants introduced into the reactor with the hydrogen. According to the teaching of U.S. Published Patent Application 2004/007366 A1, very pure hydrogen has a strong tendency to coalesce in the reaction system, with the result that the fine hydrogen bubbles combine immediately downstream of the dispersion zone to form large bubbles which have a small overall surface area. As disclosed in U.S. Published Patent Application 2004/007366 A1, this coalescence does not occur at relatively low hydrogen concentrations, the advantage of a large surface area being eliminated at too low a hydrogen concentration by too low a mass transfer.

In a particularly preferred form of the process, a sludge phase reactor is used whose gassing stirrer is present in the form of an axial conveyor, and in particular for gas/liquid dispersions, as described in, for example, EP 0 856 665 B1, which is believed to correspond to U.S. Pat. No. 6,627,174, the disclosure of which is hereby incorporated by reference.

By the particular choice of this mixing member, one achieves, on the one hand, a very high circulating capacity of the liquid phase, and on the other hand, the desired distribution of the hydrogen in the form of finely divided hydrogen bubbles in the reaction mixture is obtained in a simple manner.

As described above, local overconcentrations are to be avoided when metering the dinitrotoluenes into the reactor for the catalytic hydrogenation. Metering can be carried out via lances, nozzles or mechanically driven mixing devices. In a preferred form it is carried out via a stirring device as described in, for example, EP 1 637 220 A1, which is believed to correspond to U.S. Published Patent Application 2006/0038306, the disclosure of which is hereby incorporated by reference. This stirring device consists at least of a gassing stirrer and a blade mixer or two liquid mixers, which are arranged on a shaft and each have a feed and at least one exit opening, the exit openings of the gassing stirrer and of the liquid mixer or liquid mixers being at a defined distance from one another. In the stirring device, the ratio "a/d" of the distance "a" between the exit openings to the diameter "d" of the gassing stirrer or liquid mixer ranges from 0.025 to 0.5, preferably from 0.05 to 0.3, and the ratio "b/d" of the distance "b" between the outside edges to the diameter "d" of the gassing stirrer or liquid mixer ranges from 0.01 to 0.4, preferably from 0.02 to 0.2. The described stirring device is particularly suitable for simultaneously mixing gas and liquid phases into a reaction mixture, with optimised mixing of the phases avoiding local overconcentrations of introduced nitro group equivalents to a particular degree.

As catalysts there can be used any hydrogenation catalysts which are known to be suitable for the catalytic hydrogenation of aromatic nitro compounds. Particularly suitable are the metals of sub-group 8 of the periodic system of the elements or mixtures thereof, which can be applied, for example, to support materials such as carbon or oxides of magnesium, aluminium and/or silicon. Preference is given to the catalysts include, for example, Raney iron, cobalt and/or nickel, and in particular nickel-containing catalysts such as, for example, Raney nickel catalysts, as well as palladium- or platinum-containing catalysts on support materials. The preparation and use of such catalysts as hydrogenation catalysts of aromatic nitro compounds such as, for example, nitrobenzene, nitrotoluenes, dinitrotoluenes, chlorinated nitro aromatic compounds and others, is known and has already been described often. See, for example, EP 0 223 035 B1, EP 1 066 111 B1 and EP-A-1 512 459, which are believed to correspond to U.S. Pat. No. 4,792,626, U.S. Pat. No. 6,395,934 and U.S. Published Patent Application 2005/0107251, respectively, the disclosures of which are hereby incorporated by reference.

In a most particularly preferred embodiment of the process according to the invention there are used as catalysts the Raney nickel catalysts such as those which are described in, for example, EP-A-1 512 459, which is believed to correspond to U.S. Published Patent Application 2005/0107251, the disclosure of which is hereby incorporated by reference. As disclosed therein, the preparation of these preferred catalyst comprises 1) the melt of an alloy of from 50 to 95 wt. % aluminium, from 10 to 50 wt. % nickel, from 0 to 20 wt. % iron, from 0 to 15 wt. % cerium, cerium mixed metal, vanadium, niobium, tantalum, chromium, molybdenum or manganese and optionally also further glass-forming elements, is cooled with a cooling rate $>10^4$ K/s by pressing the molten alloy onto a rotating cooling wheel or into the gap between two cooling wheels rotating in opposite directions or by melt extraction, and 2) the rapidly solidified alloy is then subjected to treatment with organic or inorganic bases.

In comparison to conventional Raney nickel catalysts, these preferred catalysts are distinguished by a markedly increased product selectivity and catalyst working life, and particularly at reaction temperatures >120° C. Consequently, when they are used, the heat of reaction that is liberated in the hydrogenation of dinitrotoluenes can advantageously be used to produce steam for use as a heating medium.

The reaction mixture is removed from the reaction system, which is preferably operated continuously, for the catalytic hydrogenation of dinitrotoluenes according to the feeds, preferably continuously while retaining the catalyst in the system. The removal is particularly preferably carried out using cross-flow filtration, as is described in principle in, for example, EP 0 634 391 B1, which is believed to correspond to U.S. Pat. No. 5,563,296, the disclosure of which is hereby incorporated by reference, or in a specific embodiment in EP 1 137 623 B 1, which is believed to correspond to U.S. Pat. No. 6,350,911, the disclosure of which is hereby incorporated by reference. In the case of this product discharge, a partial stream is removed from the reactor and passed over a cross-flow filter, where a partial amount is removed from the product stream while the catalyst is retained, and finally the reduced partial stream "concentrated" in respect of its catalyst content is fed back to the reactor again.

The filtered product has high purity and can be processed without further chemical after-treatment to form the end product toluenediamine as described in the prior art.

In total, the process according to the invention for the preparation of toluenediamine, in which dinitrotoluene is reacted with hydrogen in the presence of at least one catalyst, is distinguished by greatly improved economy as compared with to the prior art processes. By the use of dinitrotoluene having a content of carbon dioxide in physically dissolved or chemically bonded form of less than 0.175 mol %, based on the molar amount of the dinitrotoluene used, increased catalyst selectivities and substantially improved catalyst working lives are obtained.

The process according to the invention is described in greater detail hereinbelow by means of preferred embodiments.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Description of the Analytical Method for the Quantitative Determination of Carbon Dioxide in Physically Dissolved or Chemically Bonded Form in Dinitrotoluene For the quantitative determination of physically dissolved or chemically bonded carbon dioxide in dinitrotoluene (DNT), a defined DNT sample amount is placed in a rolled-edge glass jar that can be sealed in a gas-tight manner by means of a septum, a defined amount of sulfuric acid is added, and then the amount carbon dioxide present in the gas chamber is determined by means of headspace gas chromatography (i.e. headspace analysis by means of gas chromatography) with thermal conductivity detection with calibration by an external standard.

The Following Devices are Used in the Analytical Method:
HP 5890 gas chromatograph with thermal conductivity detector (Hewlett-Packard)
HP 19 395A headspace sampler (Hewlett-Packard)

Separation Conditions:
stationary phase: silica gel #12, packed column (10 ft×⅛ in)
carrier gas: helium (flow rate of 12.5 ml/min)
column oven, temperature: 200° C.
injection block, temperature: 200° C.
detector, temperature: 250° C.
headspace cell: 45° C.
incubation time: 3.0 min
injection volume: 1 ml Completion of Quantitative Analysis:
For the analysis, 1.0 g±0.1 mg of the DNT sample were weighed into a rolled-edge glass jar. After the glass jar was sealed, 0.50 ml of sulfuric acid (w=0.330 g/kg) were injected through the septum by means of a syringe, the contents of the rolled-edge glass jar were mixed by gentle shaking, and then the rolled-edge glass jar was placed in the headspace sampler and, after tempering, analysed by means of headspace GC.

The quantitative evaluation was carried out by means of an external standard. Analogously to the analysis of the DNT sample, a defined amount of aqueous sodium hydrogen carbonate solution having a content w =0.5 g of $NaHCO_3$/kg of solution was placed in a vessel, sulfuric acid was added, and analysis was carried out by gas chromatography.

Example 1

Hydrogenation of Dinitrotoluene Having a Content of Physically Dissolved or Chemically Bonded Carbon Dioxide of 0.19 Mol % (not in Accordance with the Invention)

The laboratory hydrogenation apparatus can be operated continuously. The hydrogenation apparatus consisted of:
a heated amount of DNT covered with a layer of nitrogen,
a DNT metering pump with heated feed and discharge lines,
a one-liter hydrogenation reactor equipped with a heating/cooling jacket, an internal cooling coil and a connected heating/cooling system, a gassing stirrer, immersed metering lances and a fine-pore frit having a connected discharge line, and
a heated separator for phase separation with pressure maintenance, level measurement and heated discharge line for product removal, 800 g of a mixture containing 62% by weigh of toluenediamine and 38% by weight of water, based on 100% by weight of the mixture, were introduced, with a covering of nitrogen, into the reactor, which was preheated to 50° C., and then a suspension of 50 g of water and 7 g of a water-moist Raney nickel/iron catalyst having an iron content of 15% by weight, based on the weight of the starting alloy, was added. The closed apparatus was pressurised to 30 bar absolute with hydrogen having a purity of >99.9 vol %, and the reactor was heated to 140° C., while operating the gassing stirrer, and the desired temperature was maintained for 2 hours in order to activate the catalyst, and the atmosphere of the hydrogenation apparatus, in the pressure-bearing region, was freed of the introduced inert compounds at a purge rate of 30 standard liters/h.

125 g/h of dinitrotoluene, which was stored in the receiver at 75° C., with a content of carbon dioxide in physically dissolved or chemically bonded form of 0.19 mol %, was metered into the apparatus prepared as described above. The pressure in the system was maintained by maintaining the purge rate of 30 standard liters/h by feeding in hydrogen having a purity of >99.9 vol %, with the level in the reactor maintained at the desired level by the frit, and the discharged, catalyst-free reaction mixture was collected in the downstream separator and removed periodically therefrom to take samples.

The quality of the reaction was monitored by high-pressure liquid chromatography. After an operating time of 76 hours, complete conversion was no longer observed. At this point, the chromatograms indicated the breakthrough of nitro-amino aromatic compounds, and the test was terminated.

Example 2

Hydrogenation of Dinitrotoluene Having a Content of Physically Dissolved or Chemically Bonded Carbon Dioxide of 0.045 Mol % (According to the Invention)

The test was prepared and carried out analogously as described above in Example 1. However, a dinitrotoluene having a content of physically dissolved or chemically bonded carbon dioxide of 0.045 mol % was used.

The quality of the reaction was monitored by high-pressure liquid chromatography. Only after an operating time of 162 hours was complete conversion no longer observed, as illustrated by the chromatograms which showed the breakthrough of nitro-amino aromatic compounds. Thus, the test was terminated at that time.

Example 3

Hydrogenation of Dinitrotoluene Having a Content of Physically Dissolved or Chemically Bonded Carbon Dioxide of 0.18 Mol % (not in Accordance with the Invention)

Into a stirrer vessel that was rendered inert with nitrogen, was continuously fed 5860 kg/h of a catalyst suspension that contained 704 kg/h (about 12% by weight, based on the weight of the suspension) of a Raney nickel/iron catalyst having an iron content of about 30% by weight, based on the weight of the catalyst, and 27.1% by weight of m-TDA, 0.9% by weight of o-TDA, 37% by weight of isopropanol, 23% by weight of water, with the %'s by weight being based in each case on the total weight of the suspension. This was mixed continuously in the mixing vessel with 5876 kg of a commercial dinitrotoluene containing 99.4% by weight of dinitrotoluene, based on the weight of the mixture, in which the content of carbon dioxide in either physically dissolved or chemically bonded form of 0.18 mol %, based on the amount of dinitrotoluene used, and 5870 kg of prepared solvent containing 87% by weight of isopropanol and 13% by weight of water, based on the total weight of the prepared solvent, with the operating temperature of the mixing vessel being maintained at 75° C.

The mixture as prepared above, was removed continuously from the mixing vessel and fed to a high-pressure hydrogenation installation, where it was reacted with hydrogen at 150° C. and 100 bar in a cooled reactor cascade that was operated in series with respect to the circulated hydrogen and in parallel with respect to the dinitrotoluene mixture used. The reaction mixture left the reactor cascade after a mean dwell time of 21 minutes and was cooled to 75° C., and then fed to a phase separator, where it was separated into a gas phase and a liquid phase.

The gas phase was fed back to the start of the reactor cascade, and the hydrogen content of the gas phase was maintained at concentrations >90 vol % by a purge stream. The liquid phase was removed continuously from the separator and relieved into a stirred filtration receiver, from which it was fed to a filtration unit. In the filtration unit, the mixture was separated in such a manner that, in addition to a clear filtrate, a catalyst suspension that contained 12% by weight. of Raney nickel/iron catalyst, 27.1% by weight of m-TDA, 0.9% by weight of o-TDA, 37% by weight of isopropanol and 23% by weight of water was obtained. The clear filtrate that was separated off was processed by distillation, and the catalyst suspension produced was fed back to the mixing vessel.

The catalytic activity of the circulated catalyst was monitored by gas chromatography, and the ageing behavior of the catalyst used was taken into account by the continuous supply of a defined amount of fresh catalyst in the form of a 1% by weight of suspension in water added to the mixing vessel, and the desired concentration of the catalyst in the reaction chamber was maintained by the periodic discharge of the catalyst suspension produced in the filtration unit. The amount of fresh catalyst required to maintain the catalytic activity, based on the amount of toluenediamine prepared, was referred to as the specific catalyst consumption.

When using dinitrotoluene having a content of carbon dioxide in physically dissolved or chemically bonded form of 0.18 mol %, based on the amount of dinitrotoluene, a specific catalyst consumption of 27 g/100 kg of TDA was achieved.

Example 4

Hydrogenation of Dinitrotoluene Having a Content of Physically Dissolved or Chemically Bonded Carbon Dioxide of 0.045 Mol % (According to the Invention)

This example was carried out analogously as described above in Example 3. However, a dinitrotoluene having a content of physically dissolved or chemically bonded carbon dioxide of 0.045 mol % was used.

When using dinitrotoluene having a content of carbon dioxide in physically dissolved or chemically bonded form of 0.046 mol %, based on the amount of dinitrotoluene, a specific catalyst consumption of 6 g/100 kg of TDA was achieved.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of toluenediamine comprising reacting dinitrotoluene with hydrogen in the presence of a catalyst, wherein said dinitrotoluene has a content of carbon dioxide in physically dissolved form or chemically bonded form of less than 0.175 mol %, based on the molar amount of dinitrotoluene.

2. A process for the preparation of toluenediamine, comprising:
- a) reacting toluene with nitrating acid to form a reaction mixture comprising mononitrotoluenes,
- b) separating said reaction mixture comprising mononitrotoluenes into an organic phase comprising mononitrotoluenes and an aqueous phase comprising sulfuric acid,
- c) reacting said the organic phase comprising mononitrotoluenes with nitrating acid, to yield a reaction mixture comprising an isomeric mixture of dinitrotoluenes,
- d) separating said reaction mixture comprising an isomeric mixture of dinitrotoluenes into an organic phase comprising dinitrotoluenes and an aqueous phase comprising sulfuric acid,
- e) purifying said organic phase comprising dinitrotoluenes with water, in a multi-stage extraction in which each stage comprises mixing and phase separation, to yield an isomeric mixture of dinitrotoluenes comprising (i) from 74 to 81% by weight of 2,4-dinitrotoluene, (ii) from 17 to 21% by weight of 2,6-dinitrotoluene, and (iii) less than 5.5% by weight of the 2,3-isomer, the 2,5-isomer, the 3,4-isomer and the 3,5-isomer of dinitrotoluene, with the sum of (i), (ii) and (iii) totalling 100% by weight of dinitrotoluene,
- f) reacting said isomeric mixture of dinitrotoluenes with hydrogen, in the presence of a catalyst to form toluenediamines, wherein
- (1) the dwell time for the mixing in each stage of the multi-stage extraction in step e) is at least 4 minutes and not more than 60 minutes, and
- (2) an inert gas is additionally introduced into the mixture of the organic phase comprising dinitrotoluenes and water in at least the last stage of the extraction in step e), with the weight ratio of inert gas to dinitrotoluenes being such that the resultant purified isomeric mixture of dinitrotoluenes have a total content of carbon dioxide in physically dissolved or chemically bonded form of less than 0.175 mol %, based on the molar amount of the dinitrotoluenes.

3. The process of claim 2, wherein in e) said purifying step, alkaline water is present in at least one stage of the multi-stage extraction and neutral water is present in at least one stage of the multi-stage extraction.

4. The process of claim 1, wherein said catalyst comprises at least one nickel-containing catalyst.

5. The process of claim 2, wherein said catalyst comprises at least one nickel-containing catalyst.

* * * * *